United States Patent [19]

Hamet et al.

[11] Patent Number: 5,326,551
[45] Date of Patent: Jul. 5, 1994

[54] NUCLEAR IMAGING USES OF RADIO-LABELLED ATRIAL NATRIURETIC FACTOR

[75] Inventors: Pavel Hamet; Johanne Tremblay, both of Montréal; Raymond Lamberet, Laval; Jean Léveillé, Outremont, all of Canada

[73] Assignees: L'Istitut de Recherches Cliniques de Montreal; L'Hotel-Dieu de Montreal, Montreal, Canada

[21] Appl. No.: 634,220

[22] PCT Filed: Jun. 8, 1990

[86] PCT No.: PCT/CA90/00192

§ 371 Date: Feb. 5, 1991

§ 102(e) Date: Feb. 5, 1991

[87] PCT Pub. No.: WO90/14845

PCT Pub. Date: Dec. 13, 1990

Related U.S. Application Data

[63] Continuation-in-part of Ser. No. 363,709, Jun. 9, 1989, abandoned.

[51] Int. Cl.⁵ ............................................. A61K 49/02
[52] U.S. Cl. .................................... 424/1.45; 424/1.69
[58] Field of Search ................. 424/1.1, 9; 530/324, 530/325, 326; 930/22, 50

[56] References Cited

U.S. PATENT DOCUMENTS

| | | | |
|---|---|---|---|
| 4,609,725 | 9/1986 | Brady et al. | 530/324 |
| 4,757,048 | 7/1988 | Lewicki et al. | 530/324 X |
| 4,764,504 | 8/1988 | Johnson et al. | 530/324 X |
| 5,196,510 | 3/1993 | Rodwell et al. | 424/1.1 X |
| 5,225,180 | 7/1993 | Dean et al. | 424/1.1 |
| 5,248,764 | 9/1993 | Flanagan et al. | 530/324 |

FOREIGN PATENT DOCUMENTS 8702674 5/1987 World Int. Prop. O. .

OTHER PUBLICATIONS

Bianchi et al., "Radioautographic Localization of $^{125}$I--Atrial Natriuretic Factor in Rat Tissue," Histochemistry 1985, 82(5), 441-52. CA(103):65730c.
Kozeki et al., "Intrarenal Localization of Receptors for α-Rat Atrial Natriuretic Factor . . . ," Jpn. J. Pharmacology, 1986, 42(1), 27-33, CA(105):147037n.
Bianchi et al., "Radioautographic Localization of $^{125}$I--Labeled ANF Binding Sitos in the Brain," Neuroeadocrinology, 1986, 44(3), 365-72. CA(106):1045n.
Bianchi et al., "Localization of $^{125}$I-ANF Binding Sites in Rat Renal Medulla . . . ," J. Histochem. Cytochem., 1987, 35(2), 149-53, CA(106):96923j.
Bovy et al., "Identification of Structural Requirements for Analogues of Atrial Natriuretic Peptide (ANP) To Discriminate between ANP Receptor Subtypes," J. Med. Che., 1989, 32, 869-874.
Bovy et al., "A Synthetic Linear Secapeptide Binds to the Atrial Natriuretic Peptide Receptors and Demonstrates Cyclase Activation and Vasorelaxant Activity," The Journal of Biological Chemistry, vol. 264, No. 34, Dec. 5, 1989, 20309-20313.
Bovy, Phillippe R., "Structure Activity in the Atrial Natriuretic Peptide (ANP) Family," Medical Research Reviews, vol. 10, No. 1, 1990, 115-142.
Vlasuk et al., "Functional multiplicity of atrial natri- (List continued on next page.)

Primary Examiner—Robert L. Stoll
Assistant Examiner—John M. Covert
Attorney, Agent, or Firm—Iver P. Cooper

[57] ABSTRACT

Uptake, binding, and/or displacement of atrial natriuretic factor in a target organ of a mammal can be quantified by nuclear imaging. A diagnostically effective amount of a radio-labelled mammalian atrial natriuretic factor, active fragment or analog thereof is administered to a live mammal, and the live mammal or a portion thereof is subsequently imaged at one or more time intervals using a suitable radio-detecting device to quantify the uptake, binding and/or displacement of the radio-labelled atrial natriuretic factor, fragment or analog in one or more target organs.

41 Claims, 5 Drawing Sheets

0-5 MINS.
370 K
I 360
366 uCi

OTHER PUBLICATIONS uretic peptide receptors on cultured rat leydig tumor cells" *FEB*, vol. 228, No. 2, 290–294, 1988.

S. E. Swithers et al.; Binding sites for atrial natriuretic factor (*ANF) in kidneys and adrenal glands of spontaneously hypertensive (SHR) rats; Life Sciences 40:1673–1681 (1987).

S. Oikawa et al.; Structure of dog and rabbgit precursors of atrial natriuretic polypeptides deduced from nucleotide sequence of cloned cDNA; Biochem. and Biophys. Res. Comm. 132:3:892–899 (1985).

J. Genest et al.; The Atrial Natriuretic Factor: Its Physiology and Biochemistry; Rev. Physiol. Biochem. Pharmacol., 110:1–145 (1988).

J. R. Cusson et al.; Effects and Pharmacokinetics of Bolun Injections of Atrial Natriuretic Factor in Normal Volenteers; J. Cardiovascular Pharmacol. 11:635–642 (1988).

J. Gutkowska et al.; Circulating Forms and Radioimmunoassay of Atrial Natriuretic Factor; Endocrinology and Metabolism Clinics of North America 16(1):183–198 (1987).

P. Hamet et al.; Effect of Native and Synthetic Atrial Natriuretic Factor on Cyclic GMP; Biochem. Biophys. Res. Comm. 123(2):515–527 (1984).

J. Tremblay and P. Hamet; Cyclic GMP in Mechanism of Action of ANF in Normal and Hypertensive Cell; Medicographia 8 (3) (1986).

R. Gerzer et al.; Rapid Increase in Plasma and Urinary Cyclic GMP after Bolus Injection of Atrial Natriuretic Factor in Man; J. Clinic. Endocrine and Metabolism; 61(6):1217–1219 (1985).

R. Garcia et al.; Effect of Chronic Infusion of Synthetic Atrial Natriuretic Factor (ANF 8–33) in Conscious Two-Kidney, One-Clip Hypertensive Rats; Proc. Soc. Exp. Biol & Medicine 178:155–159 (1985).

R. Beliveau et al.; Antrial Natriuretic Factor Does Not Alter Sodium Transport in Purified Luminal Membrane from Rat Kidney Cortex; 1RCS Med. Sci. 13:402–403 (1985).

P. Larochelle et al.; Plasma Atrial Natriuretic Factor Concentrations in Essential and Renovascular Hypertension; Brit. Med. J. 294:1249–1252 (1987).

P. Larochelle et al.; Pharmacodynamic Effects of Bolus Administration of Atrial Natriuretic Factor in Normal Volunteers; Clin. Physiol. and pharmacol 451–455.

J. Tremblay and P. Hamet; Guanylate Cyclase Particulaire: L'enzyme Cible du Factor Natriuretique Auriculaire Medecine/Sciences 3:302–3 (1987).

J. Tremblay et al.; The Increase of cGMP by Atrial Natriuretic Factor Correlates with the Distribution of Particulate Guanylate Cyclase; F.E.B.S. 181(1): 17–22 (1985) and 194(2): 210–214 (1986).

P. Hamet et al.; Cyclic GMP as Mediator and Biological Marker of Atrial Natriuretic Factor; J. Hypertension 4 (suppl 2):549–556 (1986).

R. Garcia et al.; Effect of Atrial Natriuretic Factor [ANF (arg 101-Tyr 126)] on Kallikrein and Cyclic GMP in the Renovascular Hypertensive Rat; Clin. and Theory and Practice A7(11):1597–1618 (1985).

S. C. Pang et al.; Effect of Natural and Synthetic Atrial Natriuretic Factor on Arterial Blood Pressure, Natriuresis and Cyclic GMP . . . ; clinical Science 69:721–726 (1985).

P. Hamet and J. Tremblay; Aspects Physiologiques et Physiopathologiques du Facteur Natriuretique Auriculaire Nephrologie 8:7–12 (1987).

T. Maack et al.; Physiological Role of Silent Receptors of Atrial Natriuretic Factor; Sicence 238:675–678 (1987).

K. Nitta et al.; Specific Binding of Iodine-125 Labeled Atrial Natriuretic Peptide by Cultured Rat Mesangial Cells; Chemical Abstracts 105:36295a (1986).

Chem. Abs. 105(17):147037n, Koseki et al., (1986), *Jpn. J. Pharmacol*, 42(1), 27–33.

Chem Abs. 103(9):65730c, Bianchi et al., (1985), *Histochemistry*, 82(5), 441–52.

Chem. Abs. 106(13):96923j, Bianchi et al., (1987), *J. Histochem Cytochem.*, 35(2), 149–53.

Chem. Abs. 106(1):1045n, Bianchi et al., (1986) *Neuroendocrinology*, 44(3), 365–72.

*Chem. Abs* 112(7):49456y, Konrad et al., (1990), *Neuroendocrinology*, 51(3), 304–14.

*Radioautographic Localization of* $^{125}I$-Atrial Natriuretic Factor *(ANF) in Rat Tisues*, "Histochemistry", 1985, 82:441–452, bianchi, P. et al.

*Localization of Receptors for Atrial Natriuretic Polypeptide (AMP) in the Glomerulus: In Vitro Electron Microscopic Autoradiographical Investigation using* $^{125}I$-*Labeled ANP*, "Regulatory Peptides/An Intern'l Journ" vol. 21, 1988, Elsevier Sci. Publ. B.V. (Amsterdam US), Mizukawa, K. et al.

*Specific* $^{125}I$ *Brain Natriuretic Peptide-26 Binding Sites in Rat and Pig Kidneys*, "European Journal of Pharmacology", vol. 176, No. 3, Feb. 13, 1990, Maeda, T. et al.

*Autoradiographic Localization of* $^{125}I$-*Rat Atrial Natriuretic Peptide Binding Sites in Rat Brain, Adrenal Gland, and Kidney*, "Neurochemical Research", vol. 11, No. 12, Dec. 1986, Osaki, M. et al.

Flanagan, R. J. et al., "Radiolabeled Atrial Natriuretic Peptide and Somatostatin for In vivo Imaging of Receptors", in *Nuclear Imaging in Drug Discovery, Development, and Approval*, H. D. Burns et al., eds. (Birkhauser, Boston Mass.) 1993.

0-5 MINS.
370 K
I 360
366 uCi

FIG. 1 (A)

30-35 MINS.
340 K
I 390

FIG. 1 (B)

60-65 MINS.
305 K

FIG. 1 (C)

120-125 MINS.
221 K
I 395

FIG. 1 (D)

FIG. 2 (A)
LEFT KIDNEY CORTICAL REGION

FIG. 2 (B)
LEFT KIDNEY CENTRAL REGION

FIG. 2 (C)
RIGHT KIDNEY CORTICAL REGION

FIG. 2 (D)
RIGHT KIDNEY CENTRAL REGION

FIG. 3(A) LEFT KIDNEY CORTICAL REGION

FIG. 3(B) LEFT KIDNEY CENTRAL REGION

FIG. 3(C) RIGHT KIDNEY CORTICAL REGION

FIG. 3(D) RIGHT KIDNEY CENTRAL REGION

NUCLEAR IMAGING USES OF RADIO-LABELLED ATRIAL NATRIURETIC FACTOR

This application is the national stage of PCT/CA90/00192, filed Jun. 8, 1990, which is a continuation-in-part of U.S. patent application Ser. No. 07/363,709, filed Jun. 9, 1989 now abandoned.

BACKGROUND OF THE INVENTION

Specific secretory granules of mammalian atrial cardiocytes contain peptides which possess natriuretic and diuretic activities in mammals, including man. One or more peptides have been called atrial natriuretic factor (ANF) or, interchangeably, atrial natriuretic peptide (ANP). In all mammals which have been studied ANF has a similar amino acid sequence but may differ in the amino acid composition at several positions. ANF has been identified as possessing several useful anti-angiotensinogenic properties. It is an effective vasodilator, natriuretic and diuretic agent as well as having other potential activities (as further discussed below).

Atrial natriuretic factor has been isolated from both human and animal sources, and its vasodilating, natriuretic and diuretic utility has been well documented. It has also been discovered that hypertensive humans and animals respond to injection of ANF to a much greater extent than do normotensive subjects. ANF has accordingly been considered potentially useful in treating hypertension and other diseases relating to a salt-water imbalance in the body. (These properties are summarized in review articles of two of the inventors herein, Dr. Johanne Tremblay and Dr. Pavel Hamet, published in "Medicographia" (1986) 8(3) and in "Néphrologie" (1987) 8:7–12).

ANF can be radioiodinated on tyrosine residues. U.S. Pat. No. 4,609,725 (Inventors: Brady, S. F. et al) which issued on Sep, 2, 1986, relates to atrial natriuretic factor and fragments thereof. Mono-iodinated-tyrosine derivatives of these peptides and fragments are described in this patent as being useful in the study of the metabolic half-life of ANF in clinical and in vitro studies.

It is known that ANF binding or uptake is tissue specific in the body. In particular, the renal glomeruli and the distal tubule of the nephron have specific binding sites (receptor sites) for ANF. Other organs which also selectively bind ANF include blood vessels, the lungs, the brain, the heart, the outer cortex and medulla of the adrenal gland, the liver and the gonads (see J. Genest and M. Cantin: The Artial Natriuretic Factor; its Physiology and Biochemistry, in Review of Physiology, Biochemistry and Pharmacology (Genest J., Cantin M. Eds), Springer-Verlag Heidelberg, Berlin, 1988). These target organs possess more ANF receptors or binding sites than other organs.

This selective binding of ANF to target organs in humans and other mammals could be useful in the identification and diagnosis of certain conditions and pathologies, and in identifying and diagnosing anomalies of target organs. It is known that ANF receptors are abnormal in the kidney during hypertension and diabetes (see, for example, Swithers, Stewart and McCarty, Life Sci. 40, 1673 (1987)).

OBJECTS OF THE INVENTION

This invention seeks to provide a method of diagnosing or monitoring diseases in which there is a change in ANF receptor activity in a target organ by administering radio-labelled ANF (or an active fragment or analog thereof) and measuring the kinetics of binding of the radio-label in the target organ.

This invention also seeks to provide a method of diagnosing or monitoring diseases in which there is a change in ANF receptor activity in a target organ by administering radio-labelled and/or non-radio-labelled ANF (or an active fragment or analog thereof) and measuring the displacement of radio-labelled by non-radio-labelled ANF (or fragment or analog thereof).

This invention further seeks to provide compositions and kits comprising radio-labelled ANF (or an active fragment or analog thereof) which may be used in diagnosing or monitoring diseases, especially diseases of the kidneys and lungs.

SUMMARY OF THE INVENTION

Accordingly, the present invention provides a nuclear imaging method for quantifying uptake, binding, displacement or wash out of atrial natriuretic factor in target organs of mammals. In a first step, there is administered a diagnostically effective amount of radio-labelled atrial natriuretic factor or active fragment or analog to a mammal. In a subsequent step, the mammal or a portion thereof is imaged at one or more time intervals using a suitable radio-detecting device such as a gamma camera system in order to quantify the uptake, binding, displacement or wash-out of the radio-labelled atrial natriuretic factor or fragment or analog in one or more target organs.

In another aspect, the invention provides a method of diagnosing and/or monitoring diseases in which there is a decrease or increase of atrial natriuretic factor receptor binding activity in a mammalian target organ. In a first step, radio-labelled atrial natriuretic factor, an active fragment or an active modified peptide analog thereof such as 1-ortho-methoxy ANF or ANF(102-121)-des[Gln,Ser,Gly,Leu, Gly] is administered to the target organ. Subsequently, the target organ area of the body is imaged with a suitable radio-detecting device such as a gamma camera system, and the amount of radio-labelled atrial natriuretic factor, fragment or analog taken up and/or displaced by non-radio-labelled atrial natriuretic factor, is quantified.

In a further aspect, the invention provides a composition in dosage unit form for use in in vivo nuclear imaging of target organs for identifying an increase or decrease of atrial natriuretic factor receptor binding activity which comprises (a) up to 50 $\mu$g (for human applications) of radio-labelled atrial natriuretic factor, an active fragment or an analog, and (b) a suitable carrier.

In yet another aspect, the invention provides a kit containing, in separate containers, (a) mammalian atrial natriuretic factor or an active fragment or analog thereof, in lyophilized or frozen form, and (b) a diluent, together with instructions for the use thereof in the preparation of radio-labelled ANF useful for nuclear imaging target organs.

Among preferred features of the invention are the following:

(a) In the compositions referred to above, the radio-labelled ANF, active fragment or analog thereof has a specific activity between 100 Curies/m Mole and 200,000 Curies/m Mole, as well as up to 50 μg (for human applications) of the factor, fragment or analog.

(b) Target organs are preferably those which bind or accumulate ANF and can accordingly be imaged when radio-labelled. Organs such as thyroid, kidney, liver, lung, spleen and bladder are especially visualized. This also means that diseases (or treatments) which affect ANF accumulation patterns of these organs are suitable conditions for study (in addition to the disease conditions exemplified herein).

(c) Radio-labelled ANF, active fragments or analogs thereof may be administered, for example, by intravenous, intra-arterial, intrathecal, intraperitoneal or intraventricular bolus or infusion injection.

DETAILED DESCRIPTION OF THE INVENTION

In the following description of the invention, reference to ANF includes active fragments and analogs thereof. Radio-labelled ANF is administered to the human or animal subject. Administration is typically by injection, e.g., intravenous or arterial or other means of administration in a quantity sufficient to permit subsequent dynamic and/or static imaging using suitable radio-detecting devices such as a gamma camera. The amount of radio-activity that has to be administered is based on the radiodosimetry calculated, and the quantity of radio-labelled ANF injected depends in part on its specific activity of the radiolabelled ANF. In any event, the dose of ANF administered is preferably less than a significant medically effective amount. Two of the inventors earlier contributed to the discovery that a medically effective hypotensive effect in adult males (of approximately 75 kg) was obtained with a bolus injection of a dose greater than 50 μg of ANF (Cusson et al. J. Cardiovascular Pharmacol. 11: 635–642, 1988). The dose can also be described in terms of Curies per mMole and this is, in many respects, a more useful measure when imaging. Specific activities in the range of 100 Curies/mMole to 200,000 Curies/mMole of radio-labelled ANF are preferred.

Typically, the imaging is carried out on the whole body of the subject, or on that portion of the body or organ relevant to the condition or disease under study. The radio-labelled ANF produces an image of the portion of the subject in which the radio-labelled ANF has accumulated. The amount of radio-labelled ANF accumulated at a given point in time in relevant target organs can then be quantified.

Radio-labelled ANF is found to accumulate more rapidly in organs having ANF receptors, such as the organs referred to previously. After the rapid uptake of radio-labelled ANF in target organs, there follows a gradual decline in radio-label detected as the ANF is cleared from ANF receptors via the blood and ultimately the bladder before excretion.

A particularly suitable radio detecting device is a scintillation camera, such as a gamma camera. A scintillation camera is a stationary device that can be used to image distribution of radio-labelled ANF. The detection device in the camera senses the radioactive decay, the distribution of which can be recorded. Data produced by the imaging system can be digitized. The digitized information can be analyzed over time discontinuously or continuously. The digitized data can be processed to produce images, called frames, of the pattern of uptake of the radio-labelled ANF in the target organ at a discrete point in time. In most continuous (dynamic) studies, quantitative data is obtained by observing changes in distributions of radioactive decay in target organs over time. In other words, a time-activity analysis of the data will illustrate uptake through clearance of the radio-labelled ANF by the target organs with time.

It has been demonstrated that radio-labelled ANF is bound on the same receptors as is non-labelled endogenous ANF. Accordingly, radio-labelled ANF has proved useful in measuring the quantity and affinity of ANF receptor sites in subjects (see J. Genest and M. Cantin, op. cit.). It has proved an extremely useful means of investigating the regulation (up or down) of the receptors in physiological and pathological conditions of a subject's target organs over time. For this reason, it is particularly useful in identifying and diagnosing the onset and monitoring the progress of diseases which are determined to have, as one aspect, a modification in number of ANF receptors which can be transformed, by calculation, to a functional organ mass index.

The invention can be used for evaluating the glomerular mass of the kidney in diabetes and hypertension, both diseases in which glomerular mass is decreasing with the progression of the pathology. In addition, in other organs such as adrenal, the method can be used for detection of specific tumors of the outer cortex or the medulla of the adrenal by an increased mass of the target cells of ANF. In the lungs, an ANF target cell is the fibroblast and therefore increased fibroblast mass such as occurs in fibrotic disease of the lung can be detected and monitored. The morphology and patentcy of blood vessels, another target organ, can also be monitored by the method described.

ANF used in the imaging method of this invention can have a number of different chemical structures. It has been found that different mammalian species have slightly different forms of ANF, all of which have similar potency (see S. Oikawa et al: Biochem. Biophys. Res. Comm. 132:892–899, 1985). In this invention atrial natriuretic factor, an active fragment or analog thereof, is used in conjunction with an appropriate radiolabel. The atrial natriuretic factor, fragment or analog need two properties for utility in this invention. The first is a capability of binding the ANF receptor and the second is a capability of being labelled with a suitable radioisotope. Experiments were carried out using rat or human ANF or fragments (99–126 representing ANF, 101–126 representing an active fragment, and 1–98 being a pro-ANF fragment). All of the active peptide analogs of ANF which can be radio-labelled without diminished potency are also useful in this method.

Various factors should be taken into consideration in selecting an appropriate radioisotope. The radioisotope must be selected with a view to obtaining good quality resolution upon imaging, should be safe for diagnostic use in humans and animals, and should preferably have a short physical half-life so as to decrease the amount of radiation received by the body. The radioisotope used should preferably be pharmacologically inert, and, in the quantities administered, should not have any substantial physiological effect.

ANF may be radio-labelled with different isotopes of iodine, for example $^{123}I$, $^{125}I$, or $^{131}I$ (see, for example, U.S. Pat. No. 4,609,725). ANF, for use in the described method, is generally monoiodinated, but each ANF peptide may also be labelled with more than one radioisotope molecule, if required. The extent of radio-labelling must, however, be monitored, since it will affect the calculations made based on the imaging results (i.e. a diiodinated ANF will result in twice the radiation count of a similar monoiodinated ANF over the same time frame).

In applications to human subjects, it is desirable to use radioisotopes other than $^{125}$I for labelling ANF in order to decrease the total dosimetry exposure of the human body and to optimize the detectability of the labelled ANF molecule (though this radioisotope can be used if circumstances require). Ready availability for clinical use is also a factor. Accordingly, for human applications, ANF should preferably be radio-labelled with, for example, $^{67}$Ga, $^{68}$Ga, $^{90}$Y, $^{99m}$Tc, $^{111}$In, $^{113m}$In, $^{123}$I, $^{186}$Re, $^{188}$Re or $^{211}$At.

The radio-labelled ANF may be prepared by various methods. These include radio-halogenation by the chloramine - T method or the lactoperoxidase method and subsequent purification by HPLC (high pressure liquid chromatography), for example as described by J. Gutkowska et al in "Endocrinology and Metabolism Clinics of North America" (1987) 16 (1):183. Other known methods of radio-labelling can be used, such as Iodobeads TM.

There are a number of different methods of delivering radio-labelled ANF to the end-user.

It can be supplied as a "unit dose" in a physiologically suitable diluent ready for injection. For an average adult male human of about 75 kg a dose of less than about 5 milliCuries is recommended if ANF is labelled with $^{123}$I, preferably in the range of 0.3 to 5 milliCuries, particularly about 1 to 3 milliCuries. These figures are equivalent to less than about 0.067 milliCuries per kg body weight, preferably 0.004 to 0.067 milliCuries per kg body weight particularly about 0.013 to 0.04 milliCuries per kg body weight.

Alternatively, radio-labelled ANF can be supplied as a "kit" which is reconstituted prior to use. Such kit consists of a non-radioactive component, which, in this case, will be either a lyophilized or frozen form of the selected ANF, fragment or analog, and a radioactive component which is the radioisotope in a suitable diluent. The two components are appropriately combined prior to use.

DESCRIPTION OF THE DRAWINGS

In drawings which illustrate embodiments of the invention.

EXAMPLES

The following examples illustrate aspects of the invention. Experiments were conducted on a variety of mammalian species (rat, rabbit, dog and green vervet monkey) as well as on humans. The results obtained show the wide applicability of the invention.

The results obtained with the different species of mammal studied demonstrate species differences in patterns of ANF uptake and "wash-out". Adaptations of the general techniques and the protocol may be required and depend upon, among other things, the species studied, the target organs of interest and whether or not one is using the invention to diagnose disease or monitor disease and its treatment. In addition, the pattern of radiolabel uptake and "wash-out" of active ANF fragments and analogs can differ from that of ANF, for example with respect to target organs and relative uptake among different target organs.

The results also indicate that the specific activity of ANF injected affects the pattern of biodistribution.

Sources of variation among species include differences in the half-life of ANF and in the distribution and location of ANF receptor in tissues. There are at least three known receptor types and these exhibit different kinetics when tested with different ANF analogs. It will be readily appreciated that if disease affects the distribution or activity of these receptors then this adds a further variable.

MONKEY STUDIES

Example 1

ANF 99-126, rat form: 5 μg) was labelled by the inventors with $^{125}$I (1 mCi, obtained from commercial sources) using the lactoperoxidase method. The labelled compound was purified on HPLC (C-18 μBondapak TM column) by known methods. 250 μCi of the $^{125}$I ANF was administered to a 7 kg male monkey of green vervet species, as an intravenous bolus, under pentobarbital anesthesia. Prior to the experiment, the monkey was kept in a single cage with free access to food and water. The animal was subjected to data acquisition for 60 minutes using, as the scintillation detector, a gamma camera attached to a computer. Images and computer data were acquired at 10 second intervals. The results of this experiment demonstrated a concentration of radioactive decay which gave clear imaging of both kidneys and lungs.

Example 2

ANF was labelled by the inventors with $^{131}$I obtained from commercial sources. 5 μg of human ANF (99–126) with methionine in position 110 was labelled by lactoperoxidase method using 1 mCi of $^{131}$I. After iodination, the molecule was purified on HPLC by known methods.

A 7 kg anesthetized monkey which had been previously dehydrated for 18 hours was injected with an intravenous bolus injection of 80 μCi of $^{131}$I-ANF. Data acquisition with a gamma camera linked to a computer was performed (6 frames of 10 seconds were acquired followed by 30 frames of 60 seconds each). Serial images (0–5, 5–10, 10–20 min.) and time activity curves were done and analyzed of the following regions of interest: the lungs, the kidneys, the upper and lower abdomen. The results demonstrate a rapid uptake of radio-label particularly by the kidneys and lungs, followed by an uptake of radio-label in organs of the upper and lower abdomen.

Example 3

$^{131}$I-ANF prepared as described in Example 2 was used. A 7 kg anesthetized monkey was hydrated with 120 cc. of physiological saline over 30 minutes. A dose of 65 μCi of $^{131}$I-ANF was then injected intravenously and data acquisition was performed with a gamma camera attached to a computer (120 frames were acquired over 30 minutes being 1 frame per 15 seconds).

Serial images (0–7, 7–13, 13–20, 20–26, 26–30 min.) and time-activity curves were obtained and analyzed of the regions of interest over the lungs, kidneys, upper and lower abdomen. The result s of this experiment, when compared with those of Example 6, indicate a lesser uptake of radio-label in both kidney and lung of this hydrated animal when compared with the dehydrated animal of Example 2.

Example 4

$^{131}$I-ANF prepared as described in Example 2 was used. A 7 kg monkey received 100 cc. of physiological saline intravenously for a period of 40 minutes. This was followed by an intravenous bolus injection of 10 micrograms of non-radiolabelled ANF (human type) and two minutes later, 80 μCi of $^{131}$I-ANF was injected as a bolus. Data acquisition was performed with a gamma camera attached to a computer (120 frames were acquired, over 30 minutes, being 1 frame per 15 seconds).

Images (0–5, 5–10, 10–17, 17–25, 25–20 min.) and time activity curves were obtained and analyzed of the regions of interest over the lungs, the kidneys, and the upper and lower abdomen. This experiment, using a hydrated animal whose ANF receptor sites had first been challenged with unlabelled ANF, provided a model of rate of displacement of ANF on receptor sites in target organs.

Example 5

$^{123}$I-ANF prepared as in Example 2 was used. A 7.5 kg anesthetized monkey (having had free access to food and water) was injected with an intravenous bolus injection of 360 μCi of 123I-ANF (specific activity 300 Ci/mmol). Data acquisition with a gamma camera linked to a computer was performed for 3 hours (frames of 30 seconds each). Serial images of 5 minutes duration each and time activity curves were prepared and analyzed of the following regions of interest: the right and left kidneys (cortical and central regions separately). The results are summarized in FIGS. 1 and 2.

FIG. 1 consists of a selected four of the serial images, for the time periods from 0 to 5 minutes (A), from 30 to 35 minutes (B), from 60 to 65 minutes (C), and from 120 to 125 minutes (D). These images provide a visual illustration of the rapid uptake of $^{123}$I-ANF in the kidneys of the monkey in the first five minutes following injection, followed by a continuing uptake in the kidneys and lungs, and subsequently a concentration of $^{123}$I-ANF in the bladder.

Figure 1A:
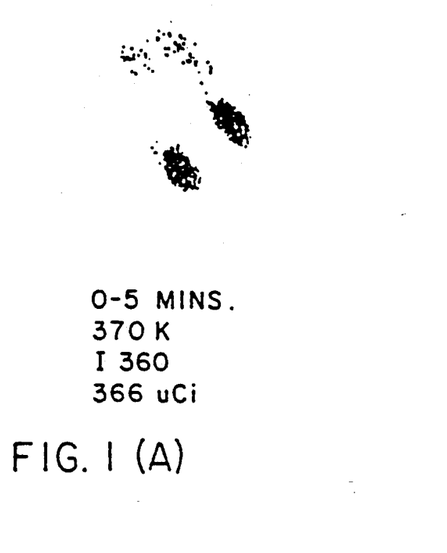
FIG. 1 is a set of serial images of five minute duration each at various time intervals, relating to an $^{123}$I-ANF studied in green vervet monkey, as follows:
(A)—0–5 minutes
(B)—30–35 minutes
(C)—60–65 minutes
(D)—120–125 minutes.
Figure 1B:
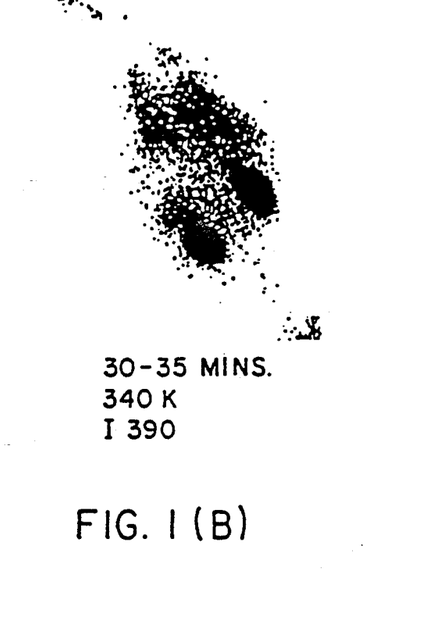
Figure 1C:
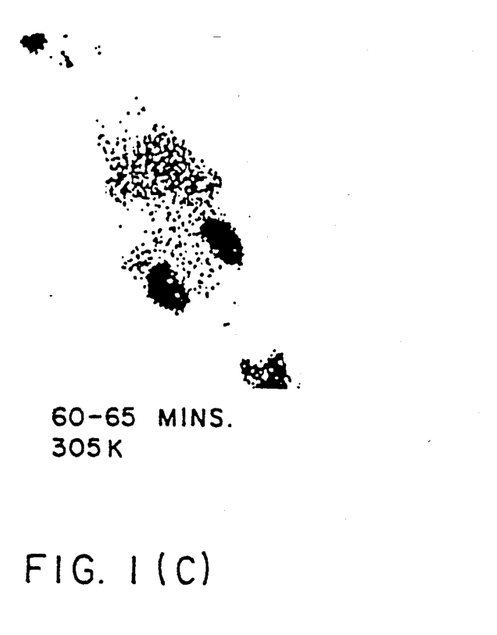
Figure 1D:
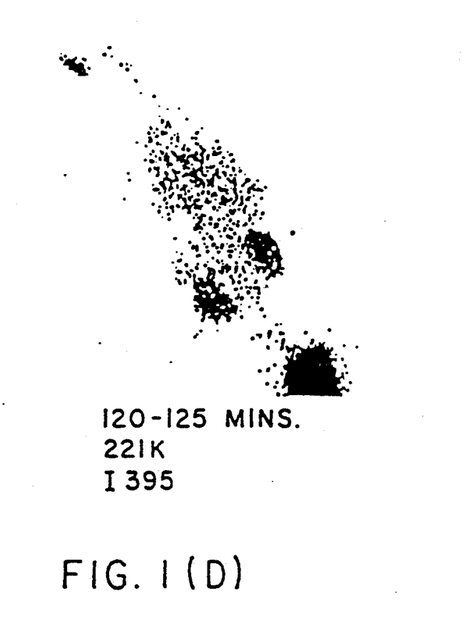
Figure 2:
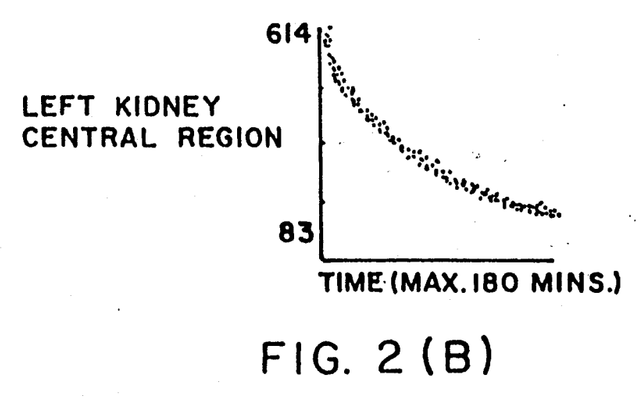
FIG. 2 is a set of graphs showing the time-activity analysis of the radio-detection of injected $^{123}$I-ANF in right and left kidney in a hydrated green vervet monkey, as follows:
(A)—cortical region of left kidney
(B)—central region of left kidney
(C)—cortical region of right kidney
(D)—central region of right kidney.

FIG. 2 is a time-activity analysis of $^{123}$I-ANF uptake in each of the cortical and central regions of each of the right and left kidney of the monkey, prepared from the data collected by the gamma camera in each 30 second interval frame. The maximum and minimum levels of radioactivity over the 3 hour test period are given in each case.

Example 6

Figure 3:
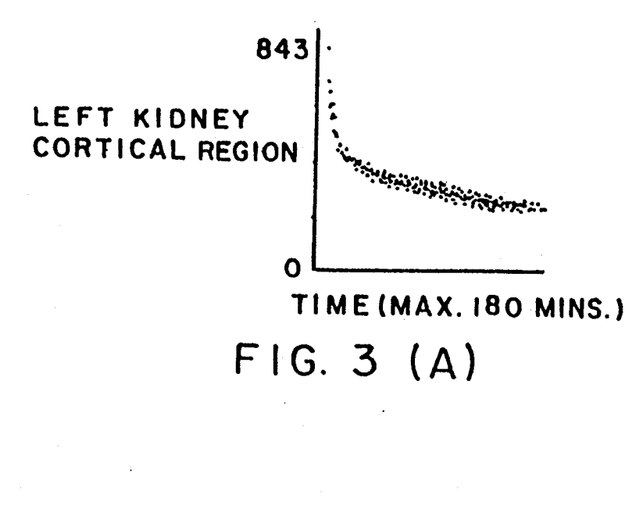
FIG. 3 is a set of graphs showing the time-activity analysis of the radio detection of injected $^{123}$I-ANF when this was preceded (5 seconds) by administration of 20 μg of non-radiolabelled ANF in the central and cortical regions of each kidney of a green vervet monkey, as follows
(A)—cortical region of left kidney
(B)—central region of left kidney
(C)—cortical region of right kidney
(D)—central region of right kidney

$^{123}$I-ANF prepared as in Example 2 was used. A 7.5 kg anesthetized monkey (having had free access to food and water) was first injected with 20 μg of non-radiolabelled ANF and 5 seconds later with 760 μCi of $^{123}$I-ANF (specific activity 300 Ci/mmol.) Data acquisition was performed as described in the Example 5. The results are summarized in FIG. 3 which shows time-activity curve analysis of $^{123}$I-ANF uptake in cortical and central regions of right and left kidney of the monkey, prepared from the data collected by the gamma camera at each 30 second interval frame. The difference in kinetics of the radiotracer between Examples 5 and 6 demonstrate that labelling with $^{123}$I-ANF is specific for ANF receptors.

RAT AND RABBIT STUDIES

Example 7

Similar experiments were conducted to show the biodistribution of labelled ANF in rats and rabbits. Some modifications were made to the specific activity of labelled ANF. Some of the rats were sacrificed so that a comparison could be made of direct radio-counting of organs and tissues with results obtained in a gamma camera study. The results obtained indicate that imaging is a good technique to use for following movements of radiolabels through organs and tissues with time.

a) Labelling Procedure

Phosphate Buffer (1.0M, pH7.0, 20 μL) was added to dry $^{123}$I-Sodium Iodide (containing 10 μMole of NaOH per 10–20 MCi) in a 250 μL V-bottom vial. The pH of this solution was checked and adjusted if necessary to between 7.0 and 8.0 with 1.ON HCl. The solution was transferred to a 1.5 mL conical polypropylene vial coated with 5 μg of freshly prepared Iodogen TM (deposited from dichloromethane). At this point carrier sodium iodide (4 ng per mCi of $^{123}$I-NaI) can be added in order to produce a final specific activity of approximately 35,000 Ci/mMole. ANF (Rat or Human, 99–126 or active-fragment 101–126, 5 μg in 5 μL of H$_2$O) was added and the solution vortexed at ambient temperature for 15 minutes. The entire reaction volume was injected onto a Waters μBondapack TM C-18 Reverse Phase HPLC Column (4.7 mm×25 cm). The solvent was a mixture of Acetonitrile in Water (0.1% Trifluoroacetic Acid) which was changed by gradient from 20% Acetonitrile to 40% over 50 minutes at 1 mL per minute. Under these conditions unlabelled ANF eluted at 23.5 minutes and $^{123}$I-ANF eluted at 29.5 minutes.

Human Serum Albumin (20mg per 2.5 mCi) was added to the eluate and the solution lyophilized. The plug was redissolved in 2 mL of Normal Saline for Injection. The saline solution was sterile filtered through a 0.22μ filter and tested for sterility and pyrogens.

Material prepared in this fashion typically had a specific activity of about 35,000 Ci/mMole and contained between 20 and 200 nanograms of ANF per dose.

The above procedure was repeated using $^{131}$I-Sodium Iodide (containing 1 μMole of NaOH per 10–20 MCi) No carrier sodium iodide was added. The reaction mixture contains some $^{131}$I-di-Iodo-ANF but the required $^{131}$I-ANF can be easily separated from this and from unreacted ANF by the same HPLC procedure described above. The specific activity of the $^{131}$I-ANF produced in this fashion is typically about 1000 Ci/mMole.

b) Rat Biodistribution Curves for $^{123}$I-ANF

A series of experiments were carried out in 150 gram female Sprague Dawley rats. The rats were injected with $^{123}$I-ANF at three different specific activities, 30,079 Curies/mmole, 3,080 Curies/mmole and 308 Curies/mmole. The animals were sacrificed at 1, 2, 5, 15 and 30 minutes post injection and dissected. The lungs, liver, kidney, muscle, thyroid and blood were collected and radioactivity counted. After correction for decay biodistribution curves were calculated (each time point representing three animals).

The biodistribution study demonstrated rapid accumulation in the lungs at 2 minutes for high specific activity material but not for low specific activity material. The same phenomenon was found in the kidneys at 4 minutes. The low specific activity material demonstrated a more rapid blood clearance up to 5 minutes at which point all three activities gave the same curve.

A gamma camera study was also carried out in similar animals using Ketamine-Rompun for anaesthesia. This showed rapid uptake in lung and kidney with maximal uptake in the kidney at 5 minutes. The bladder was obvious at 10 minutes and the throid at two hours post-injection.

c) Rabbit Biodistribution for $^{131}$I-ANF

A gamma camera study was carried out using $^{131}$I-ANF in domestic rabbits. The animals were sedated using Nembutal and the ANF was injected via the marginal ear vein. Camera images were taken at 100,000 count intervals up to 2.5 hours post injection.

A subsequent study with $^{123}$I-ANF in New Zealand White rabbits was also carried out. The animals were sedated with Nembutal and ANF was injected via the marginal ear vein. Camera images were taken at 100,000 intervals up to 1.25 hours post injection.

Both $^{123}$I-ANF and $^{131}$I-ANF demonstrated rapid accumulation in the kidney at 3 minutes post-injection. Lung was also visible but kidney was the most prominent organ.

DOG STUDIES

Example 8

A 20 kg dog, with no known previous disease and normal blood pressure was injected with 760 μCi of $^{123}$I-ANF (rat). Data acquisition with gamma camera linked to a computer was performed and analog images (one image per minute) and digital acquisition (1 frame/30 sec) were obtained for a period of 80 minutes. The dog was in prone position, anesthetized with Pentobarbital 15 minutes prior to $^{123}$I-ANF intravenous injection.

The camera was positioned posteriorly from the neck to the buttocks.

Figure 4:
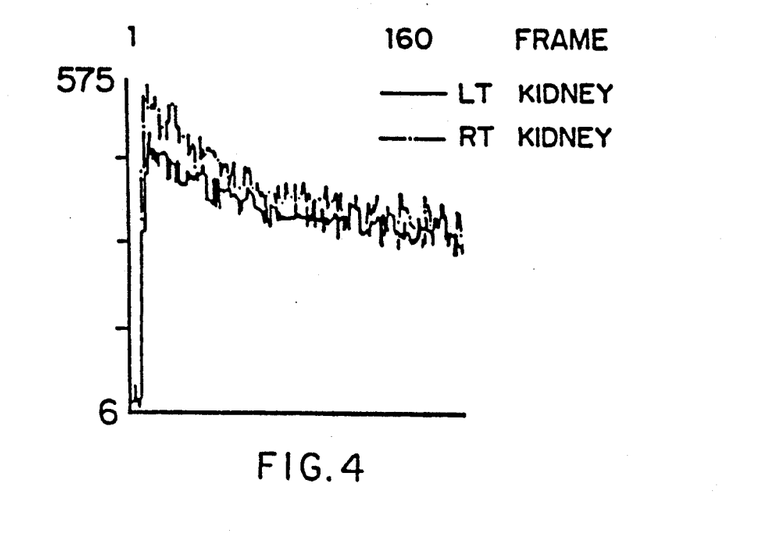
FIG. 4 is a set of graphs showing the time-activity analysis (to 80 minutes after injection) of radio-detection of $^{123}$I-ANF present in the left and right kidneys (whole organs) of a normal 20 kg dog.

Serial images, time-activity curves and several organ to organ ratios were analyzed (time-activity curves and organ to organ ratios were generated from the region of interest identified by the digital acquisition). Time activity curves for the whole kidneys are shown in FIG. 4.

Results demonstrated rapid uptake of $^{123}$I-ANF, particularly by lungs, kidney, liver and spleen, followed by other abdominal organs.

The lung uptake declined only minimally by 80 minutes, while the vizualization of spleen, liver and kidneys had by then already markedly declined.

Example 9

The same dog described in Example 8, one week after a surgical left renal artery stenosis has been performed, was studied with the same protocol used in the Example 8. The blood pressure taken several times before this experiment confirmed that the dog has developed high blood pressure (systolic blood pressure 120 mm of mercury before stenosis and 185 mm of mercury after stenosis).

Figure 5:
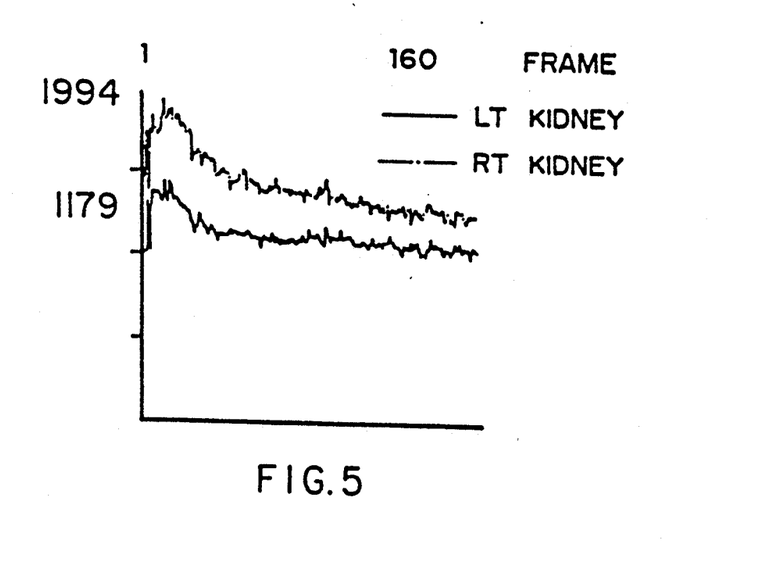
FIG. 5 is a set of graphs showing the time-activity analysis (to 80 minutes after injection) of $^{123}$I-ANF present in the left and right kidneys (whole organs) of the same dog as is exemplified in FIG. 4, subsequent to surgical left renal artery stenosis has been done and the dog had developed high blood pressure.

$^{123}$I-ANF (rat) was injected intravenously. Analysis and digital acquisition were performed as in Example 8. Time-activity curves for the kidneys of the stenotic dog are shown in FIG. 5.

Results showed rapid uptake of $^{123}$I-ANF in lungs, kidneys, liver and spleen. Lungs showed symmetrical uptake, however the kidneys showed asymmetrical uptake, the stenotic kidney showed reduced uptake when compared to the other kidney and to the lungs. Moreover, the washout of $^{123}$I-ANF from kidneys was modified and had two phases. A first wash-out phase occurred more quickly than in Example 8 for both kidneys followed by a second phase which is even slower than the one seen in Example 8. The stenotic left kidney showed reduced amplitude of the curve (indicative of lower relative uptake), a quicker first washout phase and a slower second wash-out phase than the right kidney. These results can be seen by a comparison of FIGS. 4 and 5. In FIG. 4 there is a slower washout to a first plateau (to approximately 65 to 70 minutes) compared with FIG. 5. In contrast, the washout from approximately 50 to 70 minutes to 160 minutes was less rapid (a flatter curve) in FIG. 5 when compared with FIG. 4.

Lungs, liver and spleen also showed also a time-activity curve with two phases, but the fast phase was less important than in the kidney, which suggests higher endogenous ANF levels.

In conclusion, $^{123}$I-ANF receptor in vivo imaging is able to distinguish renovascular high blood pressure from the normal condition.

HUMAN STUDIES

Examples 10 to 14 which follow show the utility of the invention in humans, more particularly the utility in the analysis of changes associated with the progress of a disease (in this case diabetes) is shown. The data which can be obtained in the methods of the invention can be used to monitor target organs as well as the progression or regression of disease in a patient, diagnose the presence of disease and indicate the type and status of the disease. Of course, the invention can also be used to study various metabolic anomalies which do not manifest themselves as disease but which affect ANF receptor type and/or biodistribution.

Example 10

A 56 kg female, with no previous disease and normal biochemistry screening test was injected with an intravenous bolus of 1030 µCi of $^{123}$I-ANF. Data acquisition with gamma camera linked to a computer was performed and analog images (one image per minute) and digital acquisition (1 frame/30 sec) were obtained for a period of 80 minutes. The camera was centred on the posterior abdomen and lower thorax for the first 80 minutes.

Serial images, time activity curves and several organ to organ ratios time activity curves were prepared and analysed. Time-activity curves and organ to organ radioactivity ratios were generated from the region of interest identified by the digital acquisition.

Results demonstrated rapid uptake of $^{123}$I-ANF, particularly by lungs, kidneys, liver and spleen, followed later by other abdominal organs.

Immediately after intravenous injection of $^{123}$I-ANF, uptake was clearly visualized in both lungs and remained perfectly visible at 80 minutes, whereas the visualization of spleen, liver and kidneys by that time, had already declined.

In spite of adequate thyroid anionic blockade with lugol solution for 4 days, the thyroid gland was well visualized within the first hour after the intravenous injection of $^{123}$I-ANF. It therefore is apparent that $^{123}$I ANF imaging of thyroid constitutes a new type of thyroid visualization independent of anionic uptake and may be therefore of clinical value in differential diagnosis and conditions with low iodine uptake such as thyroid cyst, benign or malignant tumor.

Commencing at 80 minutes, a 5 minute image was obtained for each of the head, neck, thorax and abdomen. The liver and kidneys were less well visualized than before. The bladder was visualized as radiolabelled ANF steadily accumulated there.

Example 11

A 73 kg man with no previous disease and normal biochemistry screening test was injected with 1250 µCi of $^{123}$I-ANF (intravenous bolus injection). Analog and digital acquisition were performed as in Example 10.

Results showed no significant difference from the female of Example 10 with respect to the ANF distribution ratios and curves.

At 80 minutes, a whole body scan was obtained and similarly compared to the normal female of Example 10.

These results demonstrate that nuclear imaging using labelled ANF produces similar results in men and women.

Example 12

This individual was a 80 kg male with nearly 20 years of insulin dependent diabetes and evidence of diabetic nephropathy documented by microalbuminuria but with nearly normal renal function evaluated by biochemistry test, creatinine clearance on 24-hr urine collection, DTPA-Tc$^{99m}$ renal scan and glomerular filtration rate established by DTPA-Tc$^{99m}$ plasma clearance technique.

This male was injected with an intravenous bolus of 1400 µCi of $^{123}$I-ANF. Analog images (1 image per minute) and digital acquisition (1 frame/30 seconds) were obtained for 80 minutes.

Analysis of the analog images, time activity curve and organ to organ ratios demonstrated, as compared to normal individuals, an initial uptake in kidneys that is somewhat less than in normal humans and a washout activity from the kidney that is slower as demonstrated by time activity curves and lung to kidney ratio.

At 80 min, on whole body scan, the thyroid and lungs were well visualized, and liver, spleen and kidneys presented a reduced uptake, while the bladder started to be visualized.

Example 13

This individual was a 56 kg female with a past history of 18 years of insulino-dependent diabetes with diabetic nephropathy with documented microalbuminuria. Her renal function was near normal, as established by blood biochemistry screening test, creatinine clearance on a 24-hr urine collection and glomerular filtration rate with DTPA-Tc$^{99m}$ plasma clearance technique.

The female was injected with an intravenous bolus of 1200 µCi of $^{123}$I-ANF. Analog images (1 image/minute) and digital acquisition (1 frame/30 seconds) were obtained for 80 minutes.

Result analysis was fairly similar to the male diabetic of Example 12.

At 80 min, a whole body scan was also acquired. Lungs and thyroid were still well visualized, but visualization of kidneys, liver and spleen had already declined. Bladder was faintly seen.

Example 14

A 48 kg female with a 20 year history of diabetes, treated with intensive insulin therapy which showed hyperfiltration as demonstrated by increased creatinine clearance on a 24 hr urine collection and increased glomerular filtration rate obtained by DTPA-Tc$^{99m}$plasma clearance technique. Diabetic nephropathy had also been documented by the presence of microalbuminuria.

This female was injected with an intravenous bolus of 460 µCi of $^{123}$I-ANF. Analog images (5 min/image) and digital acquisition (1 frame/minute) were obtained and then analysed.

Results demonstrated rapid uptake in lungs, kidneys, liver, spleen, followed by other abdominal organs. The washout of radioactivity of the kidneys was rapid, and radioactivity in the bladder was seen by 25 min (which is very early when compared to normal patients). The ratio of radioactivity in lung to kidney was higher at 0-5 minutes and at 55-60 minutes as compared to the normal individuals of Examples 10 and 11.

Figure 6:
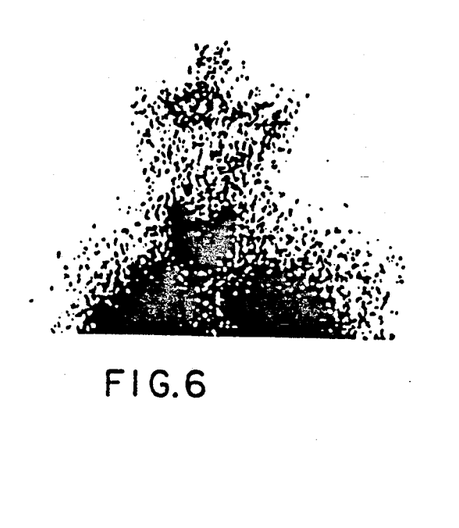
FIG. 6 is an image of the head and upper thorax of a human female with a 20 year history of diabetes after having been given an intravenous bolus of $^{123}$I-ANF.

FIG. 6 was obtained using this individual and clearly show highly selective uptake of radiolabel in the thyroid glands and lungs, especially when compared with the surrounding soft tissues. Visualization of the liver, kidneys and spleen was somewhat less intense than that of the lungs and thyroid glands.

The sequence of uptake in normal humans appears to be as follows. Initially uptake is most noticeable in the lungs and then progresses to the kidneys, liver, spleen and thyroid and thereafter to the bladder. Abnormalities in the intensity and timing of uptake often are indicative of disease. Summarizing results of Examples 10 to 14, the normal individuals showed similar results one to the other indicating that gender does not appear to be a major source of variation. The two moderately diabetic individuals of Examples, 12 and 13 showed an initial uptake of label which was lower than the normal individuals and had a slower washout from the kidneys when compared with normal individuals. The bladder was faintly seen at 80 minutes. Both individuals of Examples 12 and 13 and the normal individuals of Examples 10 and 11 can be contrasted with the individual of Example 14 who showed rapid washout of the kidneys (probably associated with hyperfiltration), as a result of which the bladder was clearly seen by 25 minutes.

In summary, the results of imaging the diabetic patients suggest that conditions of hyperfiltration as well as of decreased renal function have a distinct effect on the kinetic parameters of renal imaging with labelled ANF.

These results demonstrate the utility of the invention in species of animals widely used for research and experimental purposes as well as in humans.

Specific examples have been given in respect of a preferred nuclear imaging use of radio-labelled ANF in the visualization of target organs, in various mammals and in humans. Examples have also been given for the nuclear imaging uses of radio-labelled ANF in identifying and diagnosing anomalies of kidneys, lungs and abdomen. In particular, changes in kidney function such as might occur during hypertension and diabetes, have been studied using this procedure. It is to be understood that the same method is useful in identifying and diagnosing anomalies of other target organs in which ANF is selectively bound, including the adrenal glands, blood vessels, brain, gonads and heart.

It will be seen from the above examples that the procedure according to the invention is useful in monitoring changes in, for example, kidney function, which functional changes do occur during diseases such as hypertension and diabetes.

We claim:

1. A nuclear imaging method for quantifying uptake, binding, and/or displacement of atrial natriuretic factor in a target organ of a mammal which comprises administering a diagnostically effective amount of a radio-labelled mammalian atrial natriuretic factor, active fragment or analog thereof to a live mammal, and subsequently imaging the live mammal or a portion thereof at one or more observation times using a suitable radio-detecting device in order to quantify the uptake, binding and/or displacement of said radio-labelled atrial natriuretic factor, fragment or analog in one or more target organs.

2. The method according to claim 1 wherein the atrial natriuretic factor, fragment or analog radio-labelled with an isotope selected from $^{123}I$, $^{125}I$, $^{131}I$, $^{67}Ga$, $^{68}Ga$, $^{90}Y$, $^{111}In$, $^{113m}In$, $^{99m}Tc$, $^{186}Re$, $^{188}Re$ and $^{211}At$ is administered.

3. The method according to claim 1 wherein the atrial natriuretic factor, fragment or analog is selected from human or other mammalian atrial natriuretic factor, fragment and active analogs thereof.

4. The method according to claim 1 wherein said live mammal is a human.

5. A method according to claim 1 wherein said target organ is selected from the group consisting of thyroid gland, kidney, liver, lung, spleen and bladder.

6. A method according to claim 1 wherein said radio labelled atrial natriuretic factor, active fragment or analog thereof is administered by intravenous, intra-arterial, intrathecal, intraperitoneal, or intraventricular bolus or infusion injection.

7. The method according to claim 1 wherein the imaging is conducted at a plurality of different times on the same target organ area of the same subject.

8. The method according to claim 1 wherein the imaging is substantially continuous.

9. The method according to claim 1 wherein said imaging is conducted over substantially the entire body of said live mammal.

10. The method of claim 1 in which at least one target organ, but not the entire body is imaged.

11. In a method of diagnosing and monitoring diseases characterized by the binding of a ligand to a receptor, the improvement comprising:

administering to a live subject a radiolabeled reagent selected from the group consisting of radiolabeled atrial natriuretic factor and radiolabeled active fragments and analogues thereof, and imaging the target organ area of the live subject and determining the amount of radiation emitted by the radiolabelled reagent then present in the target organ area, which level is affected by an increase or decrease in atrial natriuretic factor receptor density or affinity in said target organ which is characteristic of said disease.

12. The method of claim 11 wherein the radiolabelled atrial natriuretic factor, fragment or analog is administered in vivo to the live subject by injection.

13. A method according to claim 11 wherein said live subject is a human.

14. A method according to claim 11 wherein said target organ is selected from the group consisting of thyroid gland, kidney, liver, lung, spleen and bladder.

15. A method according to claim 11 wherein said radio labelled atrial natriuretic factor, active fragment or analog thereof is administered by intravenous, intra-arterial, intrathecal, intraperitoneal, or intraventricular bolus or infusion injection.

16. The method according to claim 11 wherein no unlabeled reagent is administered and the labelled receptor-binding reagent competes with endogenous atrial natriuretic factor for said receptor.

17. The method of claim 11, further comprising administering an unlabeled reagent selected from the group consisting of atrial natriuretic factor and active fragments and analogues thereof.

18. The method according to claim 17 wherein said labelled reagent is administered prior to said unlabeled reagent.

19. The method according to claim 11 wherein said labelled reagent is administered after administration of said unlabeled reagent.

20. The method according to claim 11 wherein the imaging is conducted at a plurality of different times on the same target organ area of the same subject.

21. The method according to claim 11 wherein the imaging is substantially continuous.

22. The method of claim 11 in which the specific radioactivity of the radiolabeled reagent is sufficiently high as to overcome interference by ANF-degrading proteases.

23. The method of claim 11 in which the radiolabel is $^{123}I$.

24. A method of diagnosing abnormal uptake, binding and/or displacement of atrial natriuretic factor in an organ of a live mammalian subject which method comprises administering a diagnostically effective amount of radio-labelled atrial natriuretic factor, active fragment or analog thereof to said live subject and subsequently imaging the live subject or organ with a suitable radio-detecting device, quantifying the uptake, binding and/or displacement of said radio-labelled atrial natriuretic factor, active fragment or analog thereof in said organ, and comparing the uptake, binding and/or displacement of atrial natriuretic factor, active fragment or analog with the uptake, binding and/or displacement of radio-labelled atrial natriuretic factor, active fragment or analog in a reference organ in said live subject or in another live subject of the same mammal species.

25. A method according to claim 24 wherein said live subject is an human.

26. A method according to claim 24 wherein said organ is selected from the group consisting of thyroid gland, kidney, liver, lung, spleen and bladder.

27. A method according to claim 24 wherein said radio labelled atrial natriuretic factor, active fragment or analog thereof is administered by intravenous, intraarterial, intrathecal, intraperitoneal, or intraventricular bolus or infusion injection.

28. A method of diagnosing a disease state associated with an abnormal uptake, binding, and/or displacement of atrial natriuretic factor in a target organ of a mammal which comprises imaging the target organ by the method of claim 1 and correlating the observations with observations characteristic of (a) the normal state, or (b) a known disease state, of mammals of the same species.

29. The method of claim 28 in which the disease state is associated with a particular change over time in the uptake, binding, and/or displacement of atrial natriuretic factor in the target organ and the imaging observations are timed so that the disease state can be ascertained.

30. The method of claim 28 in which the target organ is the kidney.

31. The method of claim 30 in which the disease state is diabetes.

32. The method of claim 30 in which the disease state is hypertension.

33. The method of claim 28 in which the target organ is the adrenal gland.

34. The method of claim 3 in which the disease state is a cancer of the adrenal gland.

35. The method of claim 28 in which the target organ is the lung.

36. The method of claim 35 in which disease state is fibrotic disease of the lung.

37. The method of claim 28, further calculating a functional organ mass index and correlating that index with a diseased or a normal state.

38. The method of claim 28 in which said live mammal is a human.

39. The method according to claim 28 further comprising obtaining a time activity curve for the one or more target organs and correlating said time-activity curve with a disease state comparing that curve with one associated with said target organ when the animal is in (a) a normal state or (b) a particular disease state.

40. The method of claim 8 wherein said imaging is for at least about 30 minutes.

41. The method of claim 8 wherein data relating to the uptake, binding and/or displacement of atrial natriuretic factor is acquired every 10 seconds.

* * * * *

UNITED STATES PATENT AND TRADEMARK OFFICE
CERTIFICATE OF CORRECTION

PATENT NO. : 5,326,551
DATED     : July 5, 1994
INVENTOR(S) : Hamet et al

It is certified that error appears in the above-indentified patent and that said Letters Patent is hereby corrected as shown below:

Column 16, line 13,   after "claim" replace "3" with --33--.

Signed and Sealed this

Seventeenth Day of January, 1995

Attest:

BRUCE LEHMAN

Attesting Officer         Commissioner of Patents and Trademarks

UNITED STATES PATENT AND TRADEMARK OFFICE
CERTIFICATE OF CORRECTION

PATENT NO.  :  5,326,551
DATED       :  July 5, 1994
INVENTOR(S) :  HAMET et al

It is certified that error appears in the above-indentified patent and that said Letters Patent is hereby corrected as shown below:

On title page, item, [75] Inventors:,
replace "Raymond Lamberet" with --Raymond Lambert--.

Signed and Sealed this

Thirty-first Day of January, 1995

Attest:

BRUCE LEHMAN

Attesting Officer    Commissioner of Patents and Trademarks